US010435691B2

(12) United States Patent
Amrane et al.

(10) Patent No.: US 10,435,691 B2
(45) Date of Patent: Oct. 8, 2019

(54) METHODS AND PHARMACEUTICAL COMPOSITIONS FOR THE TREATMENT OF FILOVIRUS INFECTIONS

(71) Applicants: INSERM (INSTITUT NATIONAL DE LA SANTÉ ET DE LA RECHERCHE MÉDICALE), Paris (FR); UNIVERSITÉ DE BORDEAUX, Bordeaux (FR)

(72) Inventors: Samir Amrane, Pessac (FR); Jean-Louis Mergny, Pessac (FR); Amina Bedrat, Pessac (FR)

(73) Assignees: INSERM (INSTITUT NATIONAL DE LA SANTÉET DE LA RECHERCHE MÉDICALE), Paris (FR); UNIVERSITÉDE BORDEAUX, Bordeaux (FR)

( * ) Notice: Subject to any disclaimer, the term of this patent is extended or adjusted under 35 U.S.C. 154(b) by 0 days.

(21) Appl. No.: 16/184,432

(22) Filed: Nov. 8, 2018

(65) Prior Publication Data

US 2019/0062750 A1 Feb. 28, 2019

Related U.S. Application Data

(62) Division of application No. 15/557,164, filed as application No. PCT/EP2016/055089 on Mar. 10, 2016, now Pat. No. 10,160,970.

(30) Foreign Application Priority Data

Mar. 11, 2015 (EP) .................................... 15305367

(51) Int. Cl.

| | |
|---|---|
| ***C07H 21/04*** | (2006.01) |
| ***C12N 15/113*** | (2010.01) |
| ***C12N 15/115*** | (2010.01) |
| ***A61K 47/69*** | (2017.01) |
| ***A61K 38/16*** | (2006.01) |

(52) U.S. Cl.

CPC ........ *C12N 15/1131* (2013.01); *A61K 38/162* (2013.01); *A61K 47/6929* (2017.08); *C12N 15/115* (2013.01); *C12N 2310/13* (2013.01); *C12N 2310/16* (2013.01)

(58) Field of Classification Search

None

See application file for complete search history.

(56) References Cited

U.S. PATENT DOCUMENTS 8,084,433 B2 * 12/2011 Iversen ................. C12N 15/111 435/235.1

* cited by examiner

*Primary Examiner* — Kimberly Chong

(74) *Attorney, Agent, or Firm* — W&C IP

(57) ABSTRACT

The present invention relates to methods and pharmaceutical compositions for the treatment of filovirus infections. In particular, the present invention relates to a method of treating filovirus infection in a subject in need thereof comprising administering the subject with a therapeutically effective amount of at least one oligonucleotide comprising the sequence as set forth in SEQ ID NO:1 to SEQ ID NO:15.

5 Claims, 2 Drawing Sheets

Figure 1:
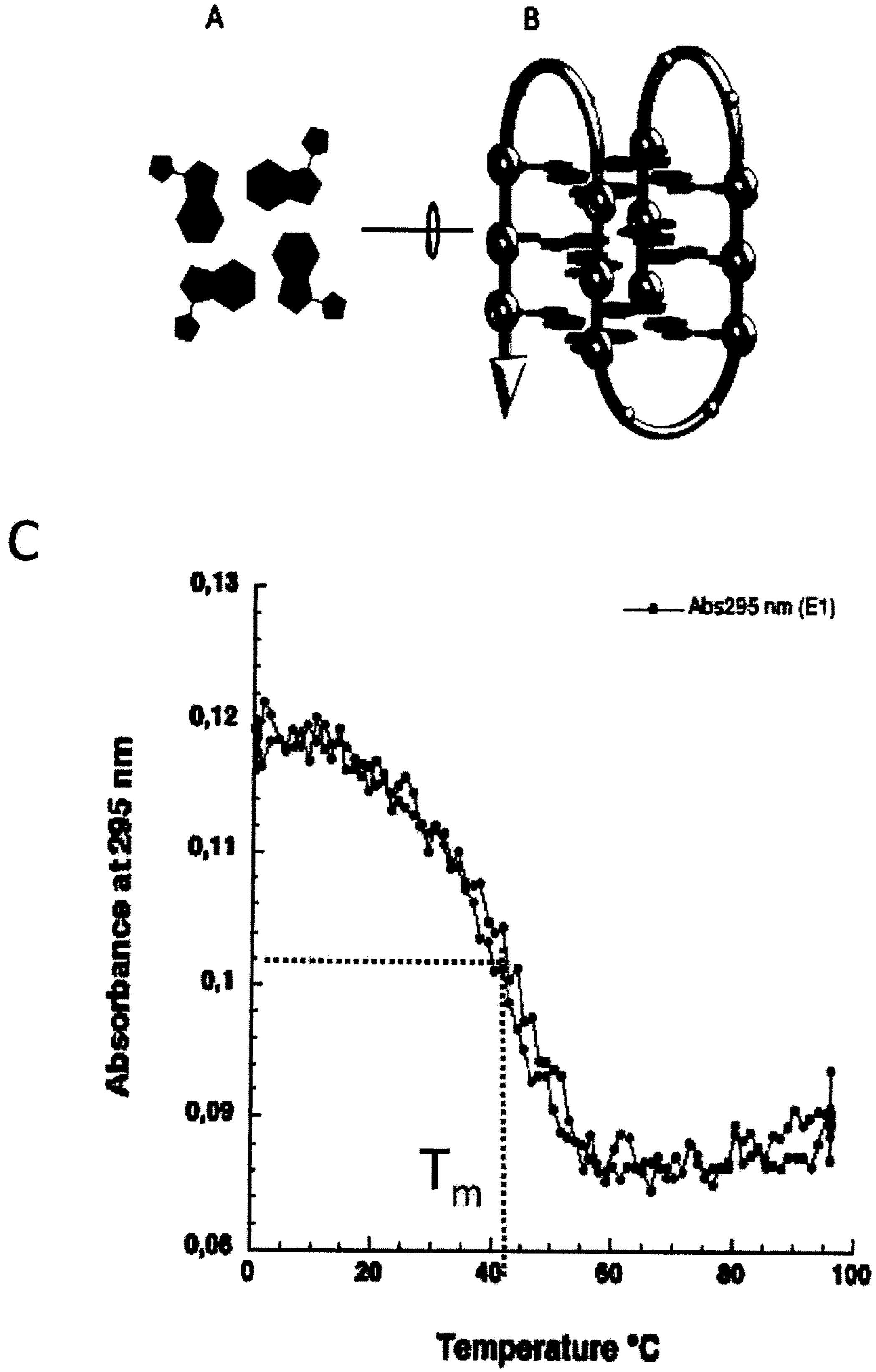

Specification includes a Sequence Listing.

SEQUENCE LISTING

```
<160> NUMBER OF SEQ ID NOS: 15

<210> SEQ ID NO 1
<211> LENGTH: 26
<212> TYPE: DNA
<213> ORGANISM: Artificial
<220> FEATURE:
<223> OTHER INFORMATION: Synthetic AS1141

<400> SEQUENCE: 1

ggtggtggtg gttgtggtgg tggtgg                                    26


<210> SEQ ID NO 2
<211> LENGTH: 25
<212> TYPE: DNA
<213> ORGANISM: Artificial
<220> FEATURE:
<223> OTHER INFORMATION: Synthetic E1

<400> SEQUENCE: 2

cggtggggcg acagtgggtg tgcgg                                     25
```

-continued

<210> SEQ ID NO 3
<211> LENGTH: 21
<212> TYPE: DNA
<213> ORGANISM: Artificial
<220> FEATURE:
<223> OTHER INFORMATION: Synthetic E2

<400> SEQUENCE: 3
cggggagtgg gccttctgga a 21

<210> SEQ ID NO 4
<211> LENGTH: 29
<212> TYPE: DNA
<213> ORGANISM: Artificial
<220> FEATURE:
<223> OTHER INFORMATION: Synthetic E3

<400> SEQUENCE: 4
gttttgggga cttgttgtgg tggcggggt 29

<210> SEQ ID NO 5
<211> LENGTH: 30
<212> TYPE: DNA
<213> ORGANISM: Artificial
<220> FEATURE:
<223> OTHER INFORMATION: Synthetic E4

<400> SEQUENCE: 5
aggggtggaa ggtttattgg gctggtattg 30

<210> SEQ ID NO 6
<211> LENGTH: 27
<212> TYPE: DNA
<213> ORGANISM: Artificial
<220> FEATURE:
<223> OTHER INFORMATION: Synthetic E5

<400> SEQUENCE: 6
aggggtcata tgggagggat tgaagga 27

<210> SEQ ID NO 7
<211> LENGTH: 18
<212> TYPE: DNA
<213> ORGANISM: Artificial
<220> FEATURE:
<223> OTHER INFORMATION: Synthetic M1

<400> SEQUENCE: 7
agagggggag gattgggc 18

<210> SEQ ID NO 8
<211> LENGTH: 20
<212> TYPE: DNA
<213> ORGANISM: Artificial
<220> FEATURE:
<223> OTHER INFORMATION: Synthetic M2

<400> SEQUENCE: 8
cgcgggttga ggaggaggga 20

<210> SEQ ID NO 9
<211> LENGTH: 28
<212> TYPE: DNA
<213> ORGANISM: Artificial
<220> FEATURE:

<223> OTHER INFORMATION: Synthetic M4

<400> SEQUENCE: 9
cggatgggct gtgggcagtg gtaaaggt 28

<210> SEQ ID NO 10
<211> LENGTH: 32
<212> TYPE: DNA
<213> ORGANISM: Artificial
<220> FEATURE:
<223> OTHER INFORMATION: Synthetic M5

<400> SEQUENCE: 10
gcgtgcttgg ttgtggtgag ggagtgggtg gc 32

<210> SEQ ID NO 11
<211> LENGTH: 25
<212> TYPE: DNA
<213> ORGANISM: Artificial
<220> FEATURE:
<223> OTHER INFORMATION: Synthetic M8

<400> SEQUENCE: 11
tgggggtggg ggagggactg gtgga 25

<210> SEQ ID NO 12
<211> LENGTH: 50
<212> TYPE: DNA
<213> ORGANISM: Artificial
<220> FEATURE:
<223> OTHER INFORMATION: Synthetic M8-1

<400> SEQUENCE: 12
caagatgttg tgcagtcgag ttgggggtgg gggagggact ggtggaatac 50

<210> SEQ ID NO 13
<211> LENGTH: 38
<212> TYPE: DNA
<213> ORGANISM: Artificial
<220> FEATURE:
<223> OTHER INFORMATION: Synthetic M9

<400> SEQUENCE: 13
agaggggact ggttggggtc tgggtggtaa atggtgga 38

<210> SEQ ID NO 14
<211> LENGTH: 30
<212> TYPE: DNA
<213> ORGANISM: Artificial
<220> FEATURE:
<223> OTHER INFORMATION: Synthetic M18-1

<400> SEQUENCE: 14
tggctgaagg ggaaggaagt ggtgctcggt 30

<210> SEQ ID NO 15
<211> LENGTH: 26
<212> TYPE: DNA
<213> ORGANISM: Artificial
<220> FEATURE:
<223> OTHER INFORMATION: Synthetic M19

<400> SEQUENCE: 15
tgaaggggaa ggaagtggtg ctcggt 26

METHODS AND PHARMACEUTICAL COMPOSITIONS FOR THE TREATMENT OF FILOVIRUS INFECTIONS

CROSS-REFERENCE TO RELATED APPLICATIONS

This application is a divisional application of U.S. Ser. No. 15/557,164, filed Sep. 11, 2017, now U.S. Pat. No. 10,160,970, which itself was a national stage filing under Rule 371, of international application PCT/EP2016/055089 filed Mar. 10, 2016, which claimed priority to European Application 15305367.3 filed Mar. 11, 2015.

FIELD OF THE INVENTION

The present invention relates to methods and pharmaceutical compositions for the treatment of filovirus infections.

BACKGROUND OF THE INVENTION

The family Filoviridae (Filovirus) is the taxonomic home of several related viruses that form filamentous infectious viral particles (virions), and encode their genome in the form of single-stranded negative-sense RNA. Two members of the family that are commonly known are Ebola virus and Marburg virus. Both viruses, and some of their lesser known relatives, cause severe disease in humans and nonhuman primates in the form of viral hemorrhagic fevers. The Ebola virus was named after the Ebola River in Zaire, Africa, near where the first outbreak was noted by Dr. Ngoy Mushola in 1976 after a significant outbreaks in both Yambuku, Zaire (now the Democratic Republic of the Congo), and Nzara, in western Sudan. There are three distinct species of Ebola virus which cause fatal disease in humans: Zaire ebolavirus (ZEBOV) (also known as EBOV), Sudan ebolavirus (SEBOV) and Ivory Coast ebolavirus (ICEBOV). Among humans, the Ebola virus is transmitted by direct contact with infected body fluids such as blood. The incubation period of Ebola virus infection varies from two days to four weeks. Symptoms are variable too, but the onset is usually sudden and characterised by high fever, prostration, myalgia, arthralgia, abdominal pains and headache. These symptoms progress to vomiting, diarrhea, oropharyngeal lesions, conjunctivitis, organ damage (notably the kidney and liver) by co-localized necrosis, proteinuria, and bleeding both internal and external, commonly through the gastrointestinal tract. Death or recovery to convalescence occurs within six to ten days of onset of symptomology. Although several antivirals have shown efficacy against Ebola virus infection in vitro or in animal models, few of them have been yet assessed in human beings with Ebola virus disease. Thus, there exists a huge need in the art for an effective curative treatment against Ebola Virus Disease.

SUMMARY OF THE INVENTION

The present invention relates to methods and pharmaceutical compositions for the treatment of filovirus infections. In particular, the present invention is defined by the claims.

DETAILED DESCRIPTION OF THE INVENTION

The present invention relates to a method of treating filovirus infection in a subject in need thereof comprising administering the subject with a therapeutically effective amount of at least one oligonucleotide comprising the sequence as set forth in SEQ ID NO:1 to SEQ ID NO:15.

The term "filovirus" refers collectively to members of the Filoviridae family of single stranded (−) RNA viruses including Ebola and Marburg viruses. As used herein, the term "Ebola virus" refers to a member of the family Filoviridae, are associated with outbreaks of highly lethal hemorrhagic fever in humans and nonhuman primates. Human pathogens include Ebola Zaire, Ebola Sudan, and Ebola Ivory Coast. Ebola Reston is a monkey pathogen and is not considered a significant human pathogen. In some embodiments of the invention, said Ebola virus is Ivory Coast Ebola virus (ICEBOV), Zaire Ebola virus (ZEBOV or EBOV), Sudan Ebola Virus (SEBOV), or a new strain or species of Ebola virus.

The method of the present invention is particularly suitable for the treatment of filovirus diseases, in particular Ebola virus disease. As used herein, the term "Ebola virus disease" (EVD), formerly known as Ebola haemorrhagic fever, is a severe, often fatal illness in humans. The incubation period, that is, the time interval from infection with the virus to onset of symptoms is 2 to 21 days. Humans are not infectious until they develop symptoms. First symptoms are the sudden onset of fever fatigue, muscle pain, headache and sore throat. This is followed by vomiting, diarrhoea, rash, symptoms of impaired kidney and liver function, and in some cases, both internal and external bleeding (e.g. oozing from the gums, blood in the stools). Laboratory findings include low white blood cell and platelet counts and elevated liver enzymes.

As used herein, the term "treatment" or "treat" refer to both prophylactic or preventive treatment as well as curative or disease modifying treatment, including treatment of subjects at risk of contracting the disease or suspected to have contracted the disease as well as subjects who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In some embodiments, the subject is infected, or is at risk of being infected with a filovirus. Diagnosis may be performed by any suitable means. One skilled in the art will understand that a subject to be treated according to the present invention may have been identified using standard tests or may have been identified, without examination, as one at high risk due to the presence of one or more risk factors (e.g., exposure to Ebola virus, etc.). In some embodiments, the subject is infected but is asymptomatic (i.e. the symptoms are not detected). In some embodiments, the diagnosis is performed by detecting filovirus virus nucleic acids in a sample obtained from the subject by any method familiar to one of skill in the art. Such methods typically include the methods based on the detecting the filovirus virus nucleic acids expression. Filovirus nucleic acids may be detected in a RNA sample, preferably after amplification. For instance, the isolated RNA may be subjected to coupled reverse transcription and amplification, such as reverse transcription and amplification by polymerase chain reaction (RT-PCR), using specific oligonucleotide primers that are specific for a filovirus nucleic acid (e.g. those encoding the nucleoprotein (NP) and the four virion structural proteins (VP40, VP35, VP30, and VP24). For instance, a RT-PCR Assay is intended for the in vitro qualitative detection of filovirus RNA in clinical specimens, including whole blood, serum, plasma, and urine, from individuals meeting filovirus clinical and/or epidemiological criteria (for example, clinical signs and symptoms associated with filovirus, contact with a probable or confirmed filovirus case, history of travel to geographic locations where filovirus cases were detected, or other epidemiologic links for which filovirus testing may be indicated as part of a public health investigation).

In some embodiments, the present invention contemplates the use of AS1411 (as described in WO2009098464) which has the sequence 5'-GGTGGTGGTGGTTGTGGTGGTGGTGG-3' (SEQ ID NO: 1) and is also known as GR026B and AGRO100. AS 1411 is a 26-mer DNA aptamer with unmodified phosphodiester linkages and forms a G-quadruplex structure (Dapic, V. et al. 2003) that is resistant to degradation by serum enzymes (Dapic, V. et al. 2002).

A further aspect of the present invention relates to an oligonucleotide comprising the sequence as set forth in SEQ ID NO:2 to SEQ ID NO:15.

For use in the instant invention, the oligonucleotide of the present invention is synthesized de novo using any of a number of procedures well known in the art. Chemical synthesis can be performed by a variety of automated nucleic acid synthesizers available in the market. These nucleic acids may be referred to as synthetic nucleic acids. Alternatively, the oligonucleotide of the present invention can be produced on a large scale in plasmids. The oligonucleotide of the present invention can be prepared from existing nucleic acid sequences using known techniques, such as those employing restriction enzymes, exonucleases or endonucleases.

In another embodiment, the oligonucleotide of the present invention is conjugated to nanoparticles to form nanoparticle-oligonucleotide conjugates. In some embodiments, the nanoparticles are metal particles such as gold, silver, copper and platinum such as described in WO2005113817, Dam et al., 2015 and Malik et al., 2015.

By a "therapeutically effective amount" is meant a sufficient amount of the oligonucleotide of the present invention to treat the Filovirus infection at a reasonable benefit/risk ratio applicable to any medical treatment. It will be understood that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific polypeptide employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The oligonucleotide of the present invention can be administered by known routes of administration including intravenous administration, intramuscular, intraperitoneal, intracerebrospinal, subcutaneous, intra-articular, intrasynovial, intrathecal, oral, topical, or inhalation routes. Effective dosages and schedules for administering antagonists or agonists are determined empirically according to guidelines generally recognized by those of skill in the art. Single or multiple dosages may be employed.

As noted above, the oligonucleotide of the present invention useful in the methods of the present disclosure can be incorporated into pharmaceutical compositions suitable for administration into an animal such as a mammal. Methods for formulating such compositions are generally well known. Guidance is available for example from Remington: THE SCIENCE AND PRACTICE OF PHARMACY, 19th Edition, Gennaro (ed.) 1995, Mack Publishing Company, Easton, Pa. Such compositions typically comprise at least one anti-RT aptamer and a pharmaceutically acceptable carrier. The term "pharmaceutically acceptable carrier" refers to any and all coatings, excipients, solvents, dispersion media, absorption delaying agents, and the like, compatible with pharmaceutical administration. Such carriers also include for example sodium chloride, colloidal silica, talc, various polymeric carriers including polyvinyl pyrrolidone, cellulose-based compounds such as carboxymethylcellulose or methylcellulose, polyvinylpyrrolidone, polyacrylates, and polyethylene glycol. Dosage forms include, for example, oral or sublingual tablets, pellets, micro- and nano-capsules, liposomes, inhalation forms, nasal sprays, and sustained-release preparations. Solutions or suspensions used for administering nucleic acids of the present invention can include one or more of the following components: a sterile diluent such as water for injection, saline solution; fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as EDTA; buffers such as acetates, citrates or phosphates and agents for the adjustment of tonicity such as sodium chloride or dextrose. In some embodiments, a pharmaceutical composition can be delivered via slow release formulation or matrix comprising nucleic acids of the present invention or DNA constructs suitable for expression of nucleic acids of the present invention in or around a site within the body.

The invention will be further illustrated by the following figures and examples. However, these examples and figures should not be interpreted in any way as limiting the scope of the present invention.

FIGURES

FIG. 1. A. Schematic representation of a tetrad composed of 4 guanine nucleosides. B. The stacking of 3 tetrads results in the formation of a G-quadruplex structure. C. Typical UV-melting profiles of G4 structure with the $T_m$ defining the specific mid-point transition.

Figure 2:
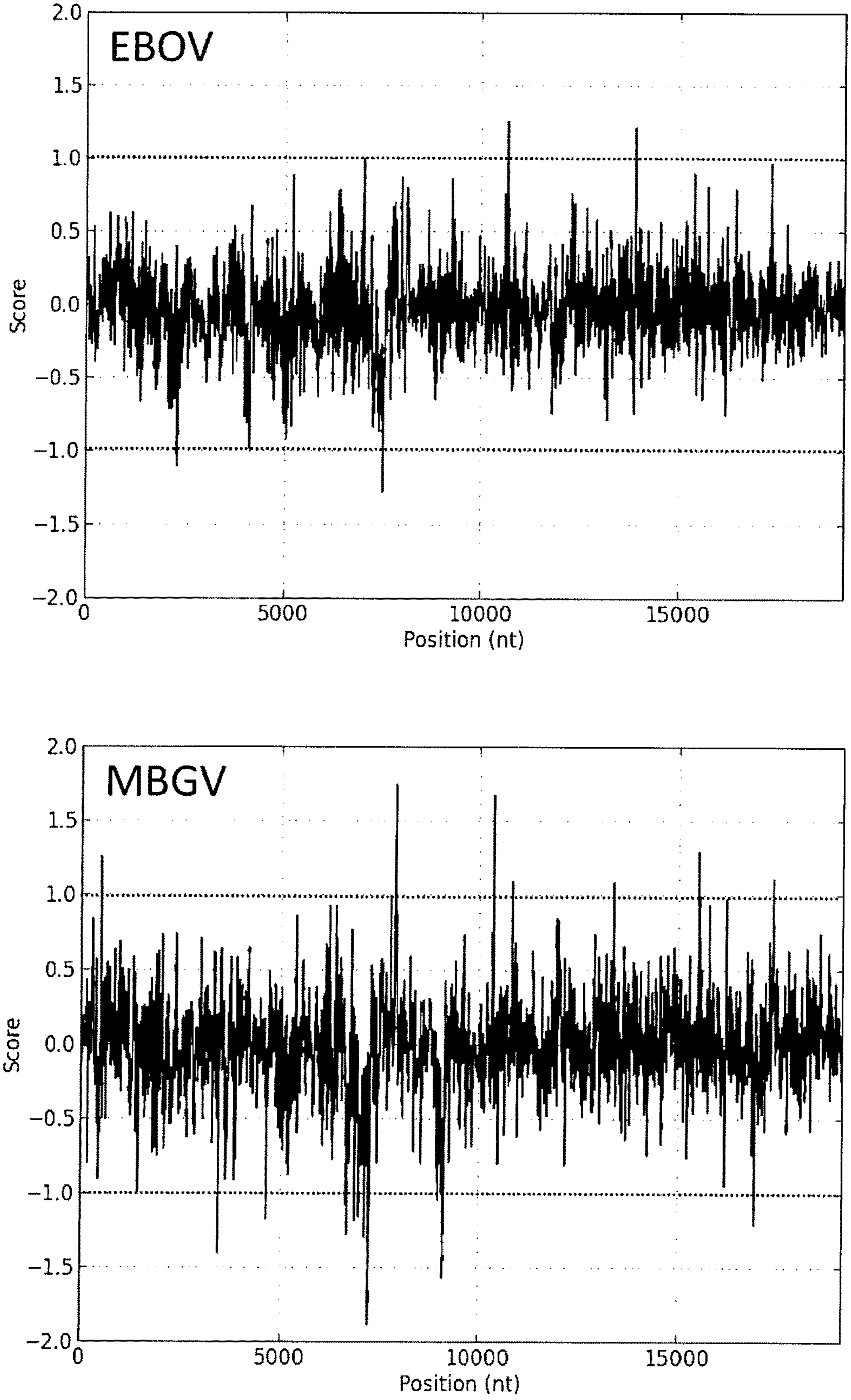

FIG. 2: Search of G4 prone sequences in EBOV and MBGV genomes. Bioinformatic search of G4 forming sequences. This graphical representation shows the average score in function of the aligned genomic sequences of from EBOV and MBGV.

EXAMPLE

Material and Methods:

Bioinformatic Analysis:

13 EBOV and 20 MBGV complete genomic sequences were extracted from the Viral Bioinformatics Resource Center. The Fasta files genomes were aligned using ClustalW program. To detect conserved G4 forming sequences in the genomes alignments we used the algorithm "G4-hunter" that we developed in the laboratory (Bedrat et al, in preparation). It searches for G/C skewness and the presence of G/C blocks in the alignment. It analyses the genome using a sliding window of 25 nucleotides and attribute a score to the first nucleotide of the window. The analysis of sequence conservation was performed using the WebLogo software to generate the LOGO representation.

Preparation of the Oligonucleotides:

Oligonucleotides were purchased from Eurogentec (Seraing, Belgium) with "Reverse-Phase Cartridge Gold purification". All oligonucleotides were dissolved in 100 μM bidistilled water and stored at −20° C. Concentrations were determined by ultraviolet (UV) absorption using the extinction coefficients provided by the manufacturer.

For the UV experiments 4 μM oligonucleotides are diluted into 10 mM lithium cacodylate buffer and 100 mM KCl.

For nuclear magnetic resonance experiments (NMR) the concentration of each samples was typically 100 μM in 20 mM potassium phosphate buffer pH 7 containing 70 mM KCl and 10% D2O.

UV-Melting Experiments:

UV-melting measurements were performed on a Uvikon XS (Secomam) UV-visible spectrophotometer coupled to a water bath temperature-control accessory. A temperature-increase rate of 0.2° C./min was applied and the absorbance values were measured every 1° C. The temperature was measured with an inert glass sensor immersed into a control quartz cell filled with water. The absorbance was monitored at 240 and 295 nm using quartz cells of 0.2 or 1 cm pathlength and 580 μl of volume. Typical UV-melting profiles of G4 structures are represented in FIG. 1C.

Results

We previously showed that G-quadruplexes oligonucleotides can act as decoys and thus are suitable for the settlement of new anti-viral strategies. This strategy was developed in the context of HIV-1 virus and several G4 sequences (EP14305763). In this strategy we showed that synthetic G4 forming oligonucleotides, derived from the HIV genome, are able to strongly inhibit HIV-1 infectivity in a viral infectivity test realized in vivo with real HIV viruses infecting HeLap4 cells. These G4s might therefore act as decoys and trap crucial proteins involved in the recognition of the same sequences present in the viral genome. We hypothesize that the presence of G4 sequences in any viral genome might reveal a potential role of these structures in the replication cycles of the virus. If this is the case, the decoy strategy we developed against HIV should also apply for the desired virus.

Using the G4-hunter algorithm we analyzed two alignments of complete genomic sequences from 13 EBOV and 20 MBGV isolates respectively. The average of the 13 or 20 scores obtained for each 25 nt window is depicted in a graphical representation (FIG. 2). We consider that the scores higher than 1 in absolute value (−1 or +1) are potentially able to form DNA or RNA G4 structures in the (−) strand (for positive values) or in the (+) strand for the negative values. Six conserved sequences from EBOV and 20 from MBGV were detected as G4 prone sequences. Thorough biophysical analysis by UV-melting experiments revealed that only 5 EBOV and 9 MBGV sequences actually formed thermodynamically stable G4s in vitro (Table 1)

CONCLUSIONS

We identified 5 EBOV and 9 MBGV G4 forming sequences. As observed for HIV virus, we hypothesize that these sequences might be recognized by viral or cellular proteins involved in important steps of EBOV and MBGV replication cycles. Therefore, as developed in the context of HIV, these oligonucleotides can be used as decoys to inhibit the viral replication of EBOV and MBGV. More generally other G4 forming sequences could also have similar anti-viral properties, in particular the AS1411 G4 forming aptamer (5'GGTGGTGGTGGTTGTGGTGGTGGTGG3') (SEQ ID NO:1) for which we showed recently some inhibitory effects on HIV replication.

TABLE 1

5 EBOV and 9 MBGV sequences actually formed thermodynamically stable G4s in vitro

| EBOV | Start/End | Strand | Sequences (5'-3') | Length | Score | $T_m$ |
|---|---|---|---|---|---|---|
| E1 | 2298-2323 | (+) | CGGTGGGGCGACAGTGGGTGT GCGG (SEQ ID NO: 2) | 25 | 1.32 | 40° C. |
| E2 | 6980-7005 | (-) | CGGGGAGTGGGCCTTCTGGAA | 21 | 1.32 | 30° C. |

TABLE 1-continued

5 EBOV and 9 MBGV sequences actually formed thermodynamically stable G4s in vitro

| | | | | | | |
|---|---|---|---|---|---|---|
| | | | (SEQ ID NO: 3) | | | |
| E3 | 7480-7509 | (+) | GTTTTGGGGACTTGTTGTGGTG GCGGGGT (SEQ ID NO: 4) | 29 | 1.41 | 35° C. |
| E4 | 10646-10678 | (-) | AGGGGTGGAAGGTTTATTGGGC TGGTATTG (SEQ ID NO: 5) | 30 | 1.23 | 30° C. |
| E5 | 13901-13930 | (-) | AGGGGTCATATGGGAGGGATT GAAGGA (SEQ ID NO: 6) | 27 | 1.41 | 20° C. |
| MBGV | Start/End | | Sequences | Length | Score | $T_m$ |
| M1 | 486-524 | (-) | AGAGGGGGAGGATTGGGC (SEQ ID NO: 7) | 18 | 1.83 | nd |
| M2 | 3423-3461 | (+) | CGCGGGTTGAGGAGGAGGGA (SEQ ID NO: 8) | 20 | 1.3 | 20° C. |
| M4 | 6642-6679 | (+) | CGGATGGGCTGTGGGCAGTGGT AAAGGT (SEQ ID NO: 9) | 28 | 1.04 | 35° C. |
| M5 | 6833-6870 | (+) | GCGTGCTTGGTTGTGGTGAGGG AGTGGGTGGC (SEQ ID NO: 10) | 32 | 1.03 | 35° C. |
| M8 | 7190-7242 | (+) | TGGGGGTGGGGGAGGGACTGG TGGA (SEQ ID NO: 11) | 25 | 2.24 | 55° C. |
| M8-1 | 7194-7242 | (+) | CAAGATGTTGTGCAGTCGAGTT GGGGGTGGGGGAGGGACTGGT GGAATAC (SEQ ID NO: 12) | 50 | 1.18 | 50° C. |
| M9 | 7848-7898 | (-) | AGAGGGGACTGGTTGGGGTCTG GGTGGTAAATGGTGGA (SEQ ID NO: 13) | 38 | 1.47 | 30° C. |
| M18-1 | 17341-17375 | (-) | TGGCTGAAGGGGAAGGAAGTG GTGCTCGGT (SEQ ID NO: 14) | 30 | 1.07 | 30° C. |
| M19 | 17346-17375 | (-) | TGAAGGGGAAGGAAGTGGTGC TCGGT (SEQ ID NO: 15) | 26 | 1.12 | 20° C. |

REFERENCES

Throughout this application, various references describe the state of the art to which this invention pertains. The disclosures of these references are hereby incorporated by reference into the present disclosure.

The invention claimed is:

1. A method of treating filovirus infection in a subject in need thereof comprising administering to the subject a therapeutically effective amount of at least one oligonucleotide comprising the sequence as set forth in SEQ ID NO:1 to SEQ ID NO:15.

2. The method of claim 1 wherein the filovirus infection is an Ebola virus infection.

3. The method of claim 2 wherein said Ebola virus is Ivory Coast Ebola virus (ICEBOV), Zaire Ebola virus (ZEBOV or EBOV), or Sudan Ebola Virus (SEBOV).

4. The method of claim 1 wherein said at least one oligonucleotide is conjugated to nanoparticles.

5. The method of claim 4 wherein said nanoparticles are gold nanoparticles.

* * * * *